(12) United States Patent
Holderle et al.

(10) Patent No.: US 9,974,902 B2
(45) Date of Patent: May 22, 2018

(54) FEEDING RATE COMPENSATED PUMP AND RELATED METHODS THEREFOR

(71) Applicant: Covidien LP, Mansfield, MA (US)

(72) Inventors: Eric Holderle, St. Louis, MO (US); Michael Justin, Kirkwood, MO (US)

(73) Assignee: KPR U.S. LLC, Mansfield, MA (US)

( * ) Notice: Subject to any disclaimer, the term of this patent is extended or adjusted under 35 U.S.C. 154(b) by 674 days.

(21) Appl. No.: 14/472,521

(22) Filed: Aug. 29, 2014

(65) Prior Publication Data

US 2015/0065988 A1 Mar. 5, 2015

Related U.S. Application Data

(60) Provisional application No. 61/871,944, filed on Aug. 30, 2013.

(51) Int. Cl.
| | | |
|---|---|---|
| *A61M 5/168* | (2006.01) | |
| *A61M 5/142* | (2006.01) | |
| *A61M 5/172* | (2006.01) | |
| *A61M 5/14* | (2006.01) | |

(52) U.S. Cl.
CPC .... *A61M 5/16886* (2013.01); *A61M 5/14232* (2013.01); *A61M 5/16827* (2013.01); *A61M 5/16877* (2013.01); *A61M 5/172* (2013.01); *A61M 2005/1403* (2013.01); *A61M 2005/14208* (2013.01)

(58) Field of Classification Search
CPC ............................ A61M 5/16827; A61M 39/04
See application file for complete search history.

(56) References Cited

U.S. PATENT DOCUMENTS

| | | |
|---|---|---|
| 4,396,385 A | 8/1983 | Kelly et al. |
| 4,474,309 A | 10/1984 | Solomon |
| 4,718,576 A | 1/1988 | Tamura et al. |
| 4,919,595 A | 4/1990 | Likuski et al. |
| 4,976,590 A | 12/1990 | Baldwin |
| 5,207,642 A | 5/1993 | Orkin et al. |
| 5,509,788 A | 4/1996 | Livingston et al. |
| 6,017,318 A | 1/2000 | Gauthier et al. |

(Continued)

OTHER PUBLICATIONS

Patent Examination Report No. 1 dated Dec. 19, 2016 in related Australian Application No. 2014312147, 4 pages.

(Continued)

*Primary Examiner* — Bhisma Mehta
*Assistant Examiner* — Matthew A Engel
(74) *Attorney, Agent, or Firm* — Adnan H. Bohri

(57) ABSTRACT

A pumping apparatus for use with a pump set to deliver fluid through the pump set to a subject includes a pumping device capable of acting on the pump set to produce a fluid flow within the pump set. A controller is in communication with the pumping device for controlling operation of the pumping device in a feeding configuration and in a flushing configuration. The controller is adapted to store a selected flow rate and a desired fluid volume of a first fluid in the memory and at least one of a flush rate and flush volume of a second fluid. A flush time compensator is capable of being run for determining a compensated feeding configuration of the first fluid based on an amount of time the controller will operate the pump device in the flushing configuration and the desired fluid volume of the first fluid.

14 Claims, 5 Drawing Sheets

(56) References Cited

U.S. PATENT DOCUMENTS

| | | | |
|---|---|---|---|
| 7,001,513 B2* | 2/2006 | Bell | A61M 1/02 210/143 |
| 7,534,099 B2* | 5/2009 | Knauper | A61M 5/14232 417/477.1 |
| 8,277,196 B2 | 10/2012 | Lewis et al. | |
| 8,360,737 B2 | 1/2013 | Smisson, III et al. | |
| 8,360,757 B2* | 1/2013 | Knauper | A61M 5/14232 417/282 |
| 8,496,606 B2* | 7/2013 | Leonard | A61M 1/14 604/4.01 |
| 8,876,793 B2* | 11/2014 | Ledford | A61M 5/14 604/513 |
| 2007/0077152 A1* | 4/2007 | Knauper | A61M 5/14232 417/44.1 |
| 2008/0119822 A1 | 5/2008 | Knauper | |
| 2009/0191066 A1* | 7/2009 | Knauper | A61M 5/14232 417/44.1 |
| 2010/0160855 A1 | 6/2010 | Bernini et al. | |
| 2012/0004779 A1* | 1/2012 | Knauper | A61M 5/14232 700/282 |
| 2012/0083760 A1* | 4/2012 | Ledford | A61M 5/14 604/500 |
| 2012/0136297 A1 | 5/2012 | Francis | |
| 2012/0191061 A1 | 7/2012 | Yodfat et al. | |
| 2015/0025453 A1* | 1/2015 | Ledford | A61M 5/14 604/67 |
| 2015/0065988 A1* | 3/2015 | Holderle | A61M 5/16877 604/500 |

OTHER PUBLICATIONS

Examiner's Report dated Jan. 24, 2017 in related Canadian Application No. 2,922,245, 3 pages.

International Preliminary Report of Patentability dated Dec. 14, 2015 in related International Application No. PCT/US2014/053338, 8 pages.

Written Opinion of the International Searching Authority dated Aug. 14, 2015 in related application PCT/US2014/053338, 6 pages.

International Search Report and Written Opinion of the International Searching Authority regarding PCT/US2014/053338, dated Dec. 2, 2014, 14 pages.

Patent Examination Report No. 2 dated Jul. 17, 2017 in related Australian Application No. 2014312147, 5 pages.

* cited by examiner

US 9,974,902 B2

FEEDING RATE COMPENSATED PUMP AND RELATED METHODS THEREFOR

CROSS-REFERENCE TO RELATED APPLICATION

This application is a non-provisional application of and claims the benefit of priority to U.S. Patent Application No. 61/871,944, titled FEEDING RATE COMPENSATED PUMP AND RELATED METHODS THEREFOR, filed on Aug. 30, 2013, which is incorporated herein by reference in its entirety for all purposes.

BACKGROUND

Field

This disclosure relates generally to pumps used to deliver nutritional liquids by way of a pump set, and more particularly to a pump that compensates for a duration of time when the pump is operating in a flush setting where nutritional liquid is not delivered to a subject or patient.

Related Art

Delivering fluids by utilizing peristaltic pumps is known. For example, administering medicine or nutrition to a subject can be effected by utilizing peristaltic flow control systems. Typically in such systems, fluid is delivered to the subject by a pump set including a flexible elastomeric tubing loaded on a flow control apparatus, such as a peristaltic pump, which delivers fluid to the subject at a controlled rate of delivery. The peristaltic pump usually has a housing that includes a rotor operatively engaged to at least one motor through a gearbox. The rotor drives fluid through the flexible tubing of the pump set by the peristaltic action effected by reversible compression created by impingement, e.g., pinching, by one or more rollers that translate by rotation of the rotor. One or more motors operatively connected to a rotatable shaft drive the rotor, which in turn progressively compresses the elastomeric tubing that drives the fluid at a controlled rate. The pump set may have a valve mechanism for permitting or preventing fluid flow communication through the pump set. The flow control system may also have a controller that operatively regulates the one or more motors which effectively controls fluid flow.

Peristaltic pumps operate by delivering fluid in small charges in aliquots. The rotor engages elastomeric tubing of the pump set, pinching off a portion of the elastomeric tubing and pushing fluid forward of the pinch point, e.g., closer to the subject than to the source of fluid toward the subject. Typically, the volume of fluid to be administered to the subject is controlled in the pump by counting the number of aliquots, each being of substantially the same volume, and stopping when the number reaches an amount corresponding to the total desired volume of fluid to be delivered. Peristaltic pumps are sanitary and generally accurate and therefore very useful in the administration of medication and therapeutic fluids to the subject. During operation of the pumps to deliver feeding fluid to the subject, it may be desirable to flush the pump set with a flushing fluid to clean out the pump set. However, incorporating a flush operation into the feeding operation affects the amount of feeding fluid delivered to the subject.

U.S. Pat. No. 4,396,385 discloses a flow metering apparatus for a fluid infusion system.

U.S. Pat. No. 4,474,309 discloses a stepping motor control procedure for achieving variable rate, quasi-continuous fluid infusion.

U.S. Pat. No. 4,718,576 discloses a fluid infusing pumping apparatus.

U.S. Pat. No. 4,919,595 discloses a fluid delivery system with deficit flow compensation.

U.S. Pat. No. 4,976,590 discloses a fluid conduit responsively adjustable pump arrangement and pump/conduit arrangement and method, and fluid conduits therefor.

U.S. Pat. No. 5,207,642 discloses a closed multi-fluid delivery system and method.

U.S. Pat. No. 5,509,788 discloses a flow-metered pumping with load compensation system and method.

U.S. Pat. No. 7,534,099 discloses an aliquot correction for feeding set degradation.

U.S. Pat. No. 8,277,196 discloses adaptive accuracy for enteral feeding pump.

U.S. Pat. No. 8,360,737 discloses dynamic range motor for a pump device.

SUMMARY

There is disclosed a pumping apparatus for use with a pump set to deliver fluid through the pump set to a subject, the pumping apparatus comprising a pumping device capable of acting on the pump set to produce a fluid flow within the pump set, and a controller in communication with the pumping device for controlling operation of the pumping device in a feeding configuration for producing flow of a first fluid in the pump set and in a flushing configuration for producing flow of a second fluid different from the first fluid in the pump set, the controller including a processor and a memory, the controller being adapted to store in the memory a selected flow rate and a desired fluid volume of the first fluid and at least one of a flush rate and flush volume of the second fluid, the controller configured to execute in the processor a flush time compensator for determining a compensated feeding configuration of the first fluid based on an amount of time the controller will operate the pump device in the flushing configuration and the desired fluid volume of the first fluid. The compensated feeding configuration can comprise a compensated flow rate of the first fluid to achieve the desired fluid volume based on the amount of time the controller will operate the pump device in the flushing configuration, the compensated flow rate being different from the selected flow rate. The flush time compensator can calculate the compensated flow rate based on the equation: $Xn=X/(1-((Y/R)/Z))$, where X is the selected flow rate, Y is a volume of the second fluid to be delivered through the pump set in the flushing configuration, R is a rate of flow for the second fluid in the flushing configuration, Z is a time interval until initiation of the flushing configuration, and Xn is the compensated flow rate. The controller can be programmed to execute the flush time compensator if the controller determines that the duration of the flushing configuration will result in a volume of the first fluid not being delivered to the subject that is equal to or greater than an acceptable threshold value of the desired fluid volume. The controller can execute the flush time compensator if the volume of first fluid not delivered to the subject is determined to be at least 5% of the desired fluid volume. The controller can be configured to output a notification perceptible to a user recommending use of the compensated feeding configuration if the volume of first fluid not delivered is equal to or greater than the acceptable threshold value. The controller can automatically use the compensated feeding configuration if the volume of first fluid not delivered is equal to or greater than the acceptable threshold value. The compensated feeding configuration can comprise a compensated flow rate, and wherein the controller is configured to operate the pumping device in a predetermined number of feeding configuration periods to deliver the desired volume of the first fluid, the controller automatically operates the pumping device in a first feeding configuration period at the selected flow rate of the first fluid and operates the pumping device in a second feeding configuration period at the compensated flow rate of the first fluid. The second feeding configuration period can be shorter than the first feeding configuration period by an amount of time the controller operates the pumping device in the flushing configuration. The flush time compensator can calculate the compensated flow rate based on a volume of the second fluid delivered through the pump set, a flow rate of the second fluid and a time interval until initiation of the next flushing configuration. The controller can be configured to receive an input for initiating the flushing configuration of the pumping device, the controller configured to execute the flush time compensator and alter operation of the pumping device in the feeding configuration after receiving the input.

There is disclosed a method of delivering fluid using a pumping apparatus that acts on a pump set attached to the pumping apparatus to produce fluid flow through the pump set for delivery of fluid to a subject, the method comprising receiving input of a selected flow rate for delivering a volume of a first fluid through the pump set to the subject; determining using computer readable instructions a duration of time for flushing the first fluid out of the pump set with a second fluid different from the first fluid; calculating using computer executable instructions a compensated flow rate for delivering the first fluid through the pump set based on the duration of time for flushing the first fluid out of the pump set; and operating the pumping apparatus to deliver the first fluid through the pump set at the compensated flow rate. The method can further comprise operating the pumping apparatus to deliver the first fluid through the pump set at the selected flow rate.

There is disclosed a method of facilitating delivery of fluid through a pump set that is operatively coupled to a pumping apparatus having a controller, the method comprising providing a memory device having computer readable instructions stored thereon that are executable by the controller, the instructions providing a flush setting adjustment factor that adjusts a flow rate of a nutritional fluid delivered through the pump set based on a function, $X_n = X/(1-((Y/R)/Z))$, where X is a selected flow rate of the nutritional fluid, Y is a volume of a flush fluid delivered through the pump set, R is a rate of flow for the flush fluid, Z is a time interval until onset of the next delivery of the flush fluid, and $X_n$ is an adjusted flow rate for the nutritional fluid.

There is disclosed a pumping apparatus for use with a pump set to deliver fluid, the pumping apparatus comprising a pump motor operatively connectable to the pump set to produce fluid flow therethrough, and a controller configured to regulate operation of the pump motor in a selected feeding configuration that produces flow of a first fluid through the pump set at a selected flow rate, regulate operation of the pump motor in a compensated feeding configuration that produces flow of a first fluid through the pump set at a compensated flow rate, and regulate operation of the pump motor in a flushing configuration that produces flow of a second fluid through the pump set, wherein the compensated flow rate of the first fluid based on the equation: $X_n = X/(1-((Y/R)/Z))$, wherein $X_n$ is the compensated flow rate of the first fluid, X is the selected flow rate of the first fluid, Y is the flush volume of the second fluid, R is a flush rate of the second fluid, and Z is a time interval until initiation of the flushing configuration. The controller can comprise a processor and a memory structure having instructions stored thereon and executable by the processor that determine a desired fluid volume of the first fluid based on the selected flow rate, determine a minimum acceptable delivery volume of the first fluid based on a product of the desired fluid volume and a tolerance factor, and determine a modified fluid volume based on the flush volume and the flush rate, wherein the processor regulates operation of the pump motor in the selected feeding configuration if the modified fluid volume is greater than the minimum acceptable delivery volume, and regulates operation of the pump motor in the compensated feeding configuration if the modified fluid volume is equal to or less than the minimum acceptable delivery volume. The tolerance factor can be at least 0.75.

Other advantages and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
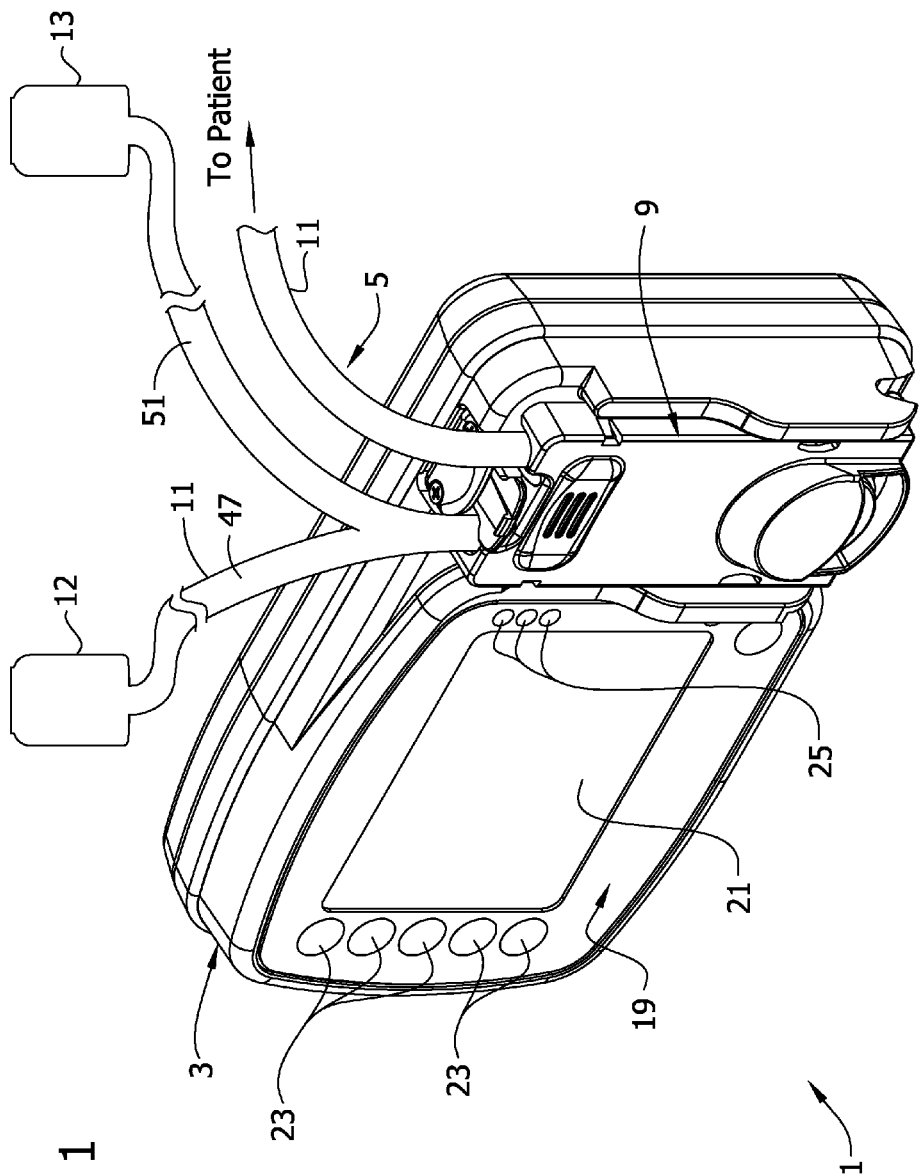
FIG. 1 is a schematic illustration showing a perspective view of a feeding pump and a fragmentary portion of a feeding set (illustrated schematically) received on the pump that may implement one or more aspects disclosed herein.

In accordance with one or more aspects, a pumping apparatus for use with a pump set to deliver fluid through the pump set to a subject includes a pumping device capable of acting on the pump set to produce a fluid flow within the pump set and a controller in communication with the pumping device for controlling operation of the pumping device in a feeding configuration for producing flow of a first fluid in the pump set and in a flushing configuration for producing flow of a second fluid different from the first fluid in the pump set, wherein the controller includes a processor and a memory, the controller being adapted to store in the memory a selected flow rate and a desired fluid volume of the first fluid and at least one of a flush rate and flush volume of the second fluid, the processor configured to retrieve instructions from the memory and execute a flush time compensator for determining a compensated feeding configuration of the first fluid based on an amount of time the controller will operate the pump device in the flushing configuration and the desired fluid volume of the first fluid. The compensated feeding configuration can include a compensated flow rate of the first fluid to achieve the desired fluid volume based on the amount of time the controller will operate the pump device in the flushing configuration. The compensated flow rate is typically different from the selected flow rate. The flush time compensator can calculate the compensated flow rate based on the equation: $X_n = X/(1-((Y/R)/Z))$, where X is the selected flow rate, Y is a volume of the second fluid to be delivered through the pump set in the flushing configuration, R is a rate of flow for the second fluid in the flushing configuration, Z is a time interval until initiation of the flushing configuration, and $X_n$ is the compensated flow rate. The controller can be programmed to execute the flush time compensator if the controller determines that the duration of the flushing configuration will result in a volume of the first fluid not being delivered to the subject that is equal to or greater than an acceptable threshold value of the desired fluid volume. The controller can execute the flush time compensator if the volume of first fluid not delivered to the subject is determined to be at least 5% of the desired fluid volume. The controller can be configured to output a notification perceptible to a user recommending use of the compensated feeding configuration if the volume of first fluid not delivered is equal to or greater than the acceptable threshold value. The controller can automatically use the compensated feeding configuration if the volume of first fluid not delivered is equal to or greater than the acceptable threshold value. The compensated feeding configuration can include a compensated flow rate. In still certain embodiments. The controller can be configured to operate the pumping device in a predetermined number of feeding configuration periods to deliver the desired volume of the first fluid. The controller can automatically operate the pumping device in a first of the periods at the selected flow rate of the first fluid and operates the pumping device in a second of the periods at the compensated flow rate of the first fluid. The second feeding configuration period can be shorter than the first feeding configuration period by an amount of time the controller operates the pumping device in the flushing configuration. The flush time compensator can calculate the compensated flow rate based on a volume of the second fluid delivered through the pump set, a flow rate of the second fluid and a time interval until initiation of the next flushing configuration. The controller can be configured to receive user input for initiating the flushing configuration of the pumping device. The flush time compensator can alter operation of the pumping device in the feeding configuration after receiving the user input. The first fluid can be a nutritional liquid and the second fluid is water. The memory can be selected from a group consisting of: random access memory, flash, EEPROM, PROM, and disk.

In accordance with one or more aspects, a method of delivering fluid using a pumping apparatus that acts on a pump set attached to the pumping apparatus to produce fluid flow through the pump set for delivery of fluid to a subject. The method can involve receiving input of a selected flow rate for delivering a volume of a first fluid through the pump set to the subject, determining using computer readable instructions a duration of time for flushing the first fluid out of the pump set with a second fluid different from the first fluid, and calculating using computer executable instructions a compensated flow rate for delivering the first fluid through the pump set based on the duration of time for flushing the first fluid out of the pump set. In some cases, the method can further involve operating the pumping apparatus to deliver the first fluid through the pump set at the compensated flow rate. The method can further include operating the pumping apparatus to deliver the first fluid through the pump set at the selected flow rate.

In accordance with one or more aspects, a computer-readable medium having computer-executable instructions stored thereon that perform a method of delivering fluid through a pump set that is operatively coupled to a pumping apparatus. The instructions can provide a flush setting adjustment factor that adjusts a flow rate of a nutritional fluid delivered through the pump set based on a function, $X_n$=X/(1−((Y/R)/Z)), where X is a selected flow rate of the nutritional fluid, Y is a volume of a flush fluid delivered through the pump set, R is a rate of flow for the flush fluid, Z is a time interval until onset of the next delivery of the flush fluid, and $X_n$ is an adjusted flow rate for the nutritional fluid.

In accordance with one or more aspects, a pumping apparatus for use with a pump set to deliver fluid. The pumping apparatus can comprise a pumping device configured to act on the pump set to produce fluid flow therethrough; and a controller configured to regulate operation of the pumping device in a selected feeding configuration that produces flow of a first fluid through the pump set at a selected flow rate, regulate operation of the pumping device in a compensated feeding configuration that produces flow of a first fluid through the pump set at a compensated flow rate, and regulate operation of the pumping device in a flushing configuration that produces flow of a second fluid through the pump set, wherein the compensated flow rate of the first fluid based on the equation:

$$X_n = \frac{X}{\left(1 - \frac{\left(\frac{Y}{R}\right)}{Z}\right)},$$

wherein Xn is the compensated flow rate of the first fluid, X is the selected flow rate of the first fluid, Y is the flush volume of the second fluid, R is a flush rate of the second fluid, and Z is a time interval until initiation of the flushing configuration. The controller can comprise a processor; and a memory structure having instructions stored thereon and executable by the processor that determine a desired fluid volume of the first fluid based on the selected flow rate, determine a minimum acceptable delivery volume of the first fluid based on a product of the desired fluid volume and a tolerance factor, and determine a modified fluid volume based on the flush volume and the flush rate, wherein the processor regulates operation of the pump motor in the selected feeding configuration if the modified fluid volume is greater than the minimum acceptable delivery volume, and regulates operation of the pump motor in the compensated feeding configuration if the modified fluid volume is equal to or less than the minimum acceptable delivery volume. The tolerance factor can be at least 0.75.

Figure 2:
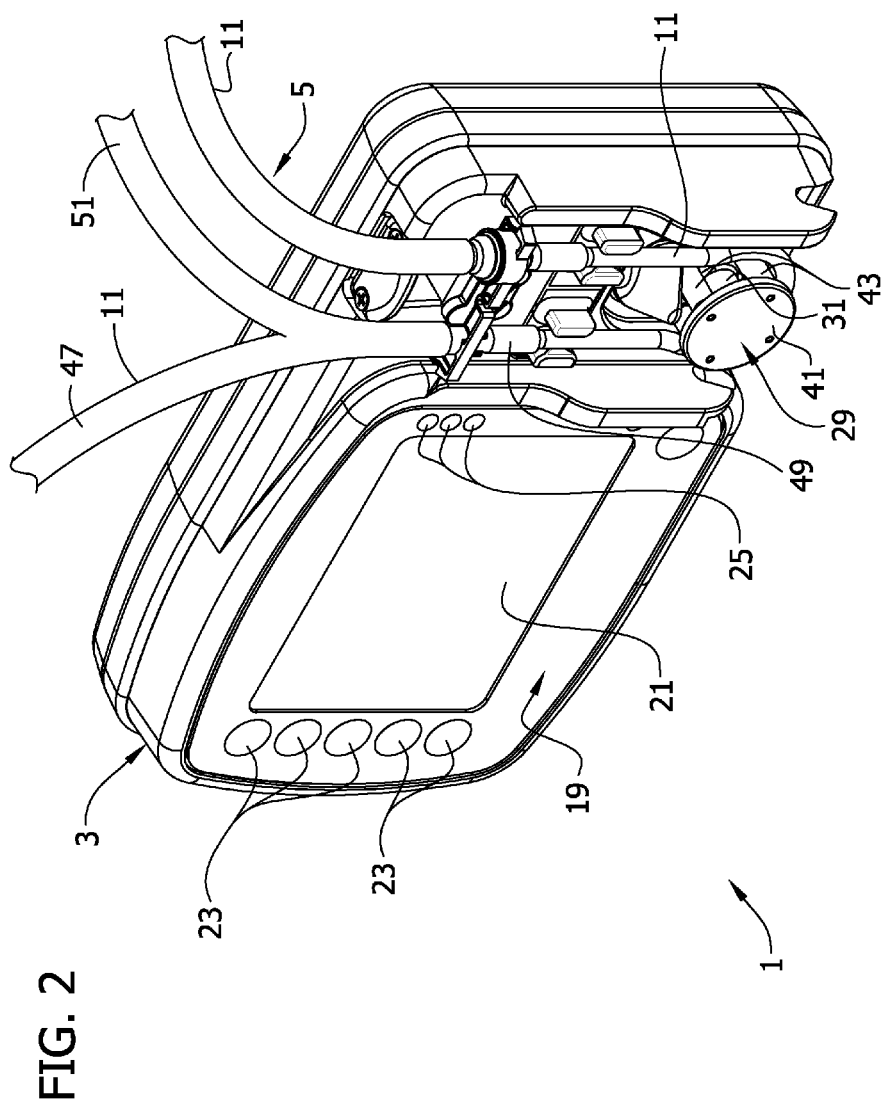
FIG. 2 is a schematic illustration showing a perspective view of the pump of FIG. 1 with a cassette housing of the feeding set removed.
Figure 3:
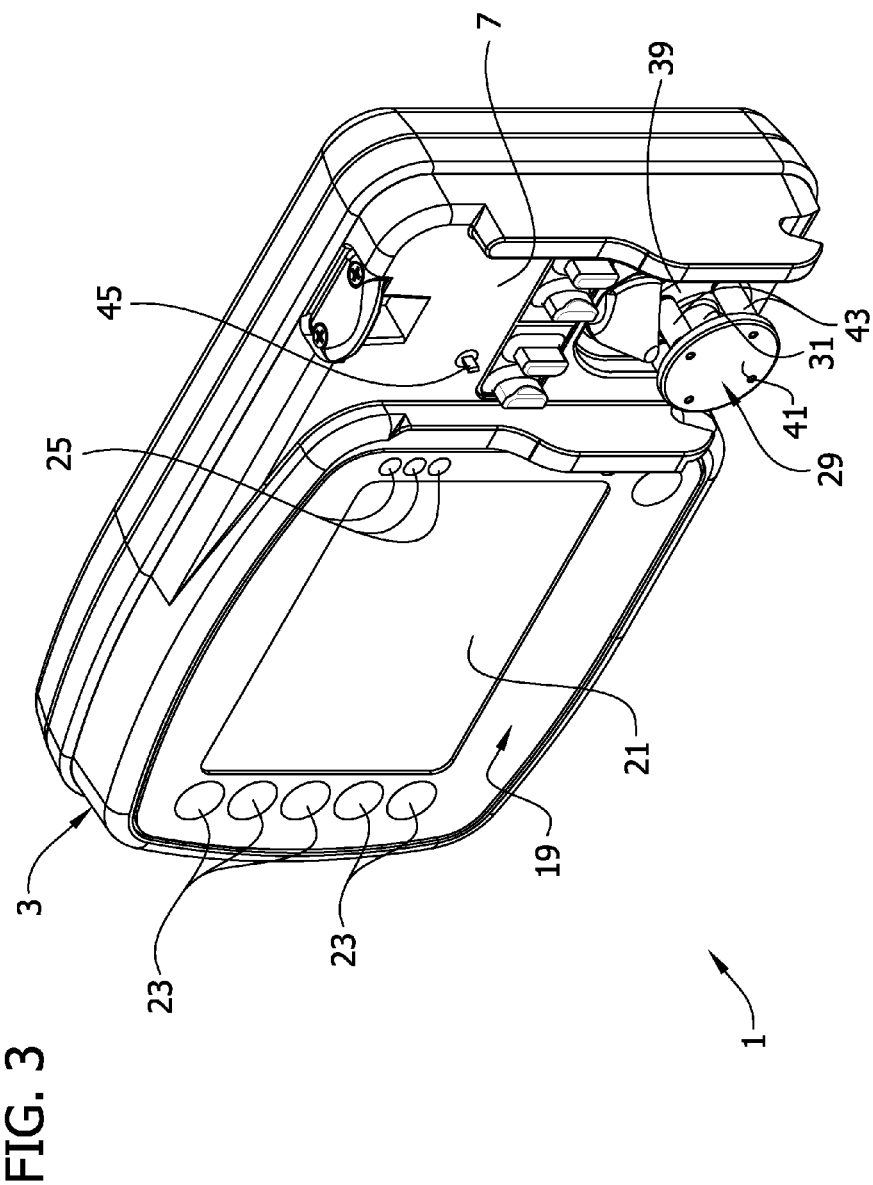
FIG. 3 is a schematic illustration showing a perspective of the pump of FIG. 1, without the feeding set.

Referring now to the exemplary embodiment schematically illustrated in FIGS. 1-3, an enteral feeding pump as a pumping apparatus is generally indicated at 1. The pump 1 may comprise a housing 3 that is constructed so as to allow an administration feeding set 5 (broadly, "a pump set") to be loaded or mounted to the housing. The housing 3 may comprise a recess 7 (FIG. 3) for receiving a cassette 9 of the feeding set 5 to load the feeding set on the pump. The administration feeding set 5 can comprise tubing, e.g., flexible elastomeric tubing, indicated generally at 11 that provides a fluidic pathway between a bag 12 of a first fluid, such as a nutritional liquid (broadly, "a feeding fluid source") and a subject or patient (FIG. 1). The tubing 11 may also provide a fluidic pathway between a bag 13 of a second fluid such as a flushing liquid (broadly, "a flushing liquid source") and the subject. In one embodiment the flushing liquid may be water, and the nutritional liquid may be a nutritional formula. The bags 12, 13 are shown schematically in FIG. 1. The cassette 9 may mount the tubing 11 for engaging the tubing with the pump 1 when the cassette is received in the recess 7. It will be understood that a pump set may have a construction other than shown herein without departing from the scope of the present disclosure. For example a pump set (not shown) may not include a cassette 9 as illustrated herein. Thus, some aspects may be advantageously incorporated into peristaltic type flow control apparatus that controls delivery of the first fluid and controls flow of the second fluid. Further, one or more of the disclosed features and aspects may be implemented in other non-peristaltic flow control apparatus that delivers a first fluid and utilizes a flushing or second fluid.

As used herein, the term "load" means that the tubing 11 is engaged with the pump 1 so that the administration feeding set 5 is ready for operation with the pump to deliver fluid to a subject. It will be appreciated that the term "housing," as used herein, may include many forms of supporting structures including, without limitation, multi-part structures and structures that do not enclose or house the working components of the pump 1.

The pump 1 may include a user interface 19 with a display screen indicated at 21 on the front of the housing 3 that is capable of displaying information about the status and operation of the pump. The pump 1 can further comprise buttons 23 and light emitting diodes 25 on the housing 3 for use with the display screen 21 to facilitate exchanging information, such as providing and obtaining information, between the pump 1 and a user. Various user interfaces for displaying information to the user and receiving user input may be implemented. Any of the various configurations of the user interface can involve utilizing one or more graphical display subcomponents. As an example, the display screen 21 may be a graphical user interface having a touch screen by which the user can provide the input information. In other embodiments, the user interface can be a tethered component that can be used to provide input information, provide operating information pertaining to the flow control apparatus, or both, e.g., to input operating parameters and type of fluid information. Still other variants can involve utilizing remote input and output subsystems to facilitate exchange of the information. For example, the pump 1 may be connected to a remote user interface (not shown) with at least one output device such as display screen and to at least one input device such as a keyboard by a tether to facilitate the data exchange. In other cases, the user interface can be in wireless communication with the pump through, for example, any one or more of a wireless local area network, a wide area network, and a cellular communication system. In still other cases, the pump may have at least one of a visible and an audible output device that provide a notification that is perceptible by the subject or a user of the pump, which can provide an indication or recommendation to initiate or use the compensated feeding configuration if, for example, the volume of the first fluid not delivered is or is expected to be equal to or greater than an acceptable threshold value.

Figure 4:
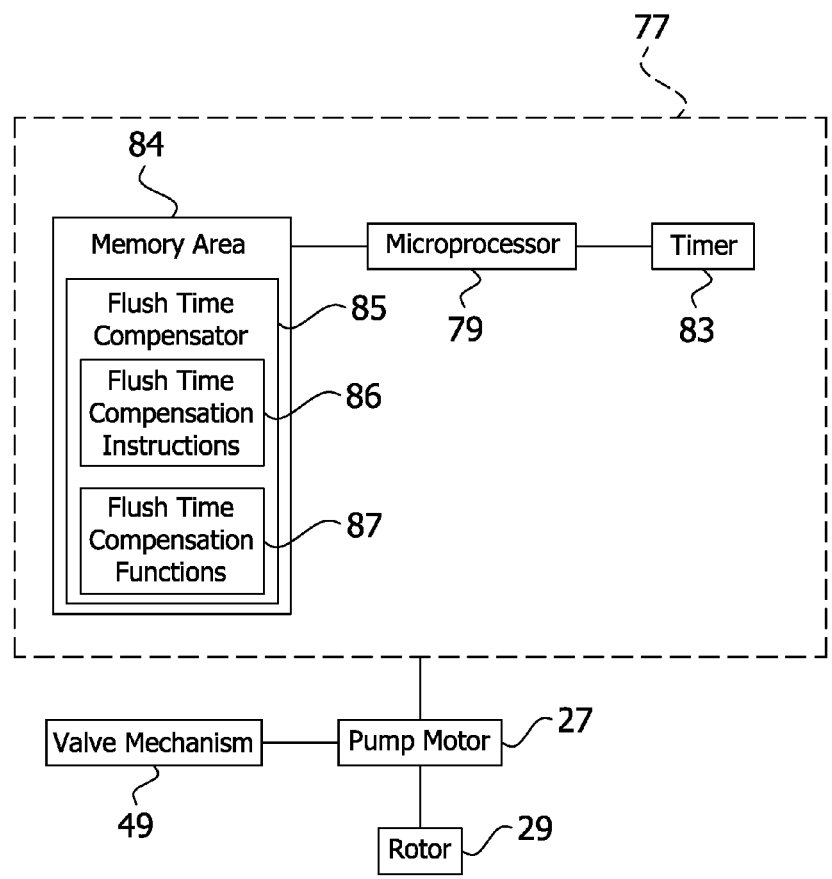
FIG. 4 is a block diagram of showing components of the feeding pump that may be utilize to implement one or more aspects disclosed herein.

Referring to FIGS. 2-4, the pump 1 may include a pump motor 27 (FIG. 4) located in the housing 3. A pump rotor 29 may be mounted on a rotatable shaft 31 and rotated by the motor 27. In one embodiment, the pump rotor 29 includes an inner disk 39, an outer disk 41, and preferably a plurality of rollers 43 mounted between the inner and outer disks rotatable about their longitudinal axes relative to the disks. The motor 27 may also be connected to a valve shaft 45 (FIG. 3). It will be understood that the valve shaft 45 could be omitted, or a separate motor (not shown) could be provided to operate the valve shaft. The rollers 43 may engage the administration feeding set 5 for moving fluid through the feeding set. In the illustrated embodiment, the pump motor 27, rotatable shaft 31, rotor 29, and valve shaft 45 may broadly be considered "a pumping device". It will be understood that peristaltic pumps that use mechanisms other than rollers may fall within the scope of the present disclosure. For example, a linear peristaltic pump could be used to incorporate one or more aspects or features disclosed herein. In other cases, the pumping device may be considered as only the peristaltic subsystem, without necessarily involving the valve shaft.

Referring to FIGS. 1, 2 and 4, the tubing 11 of the administration feeding set 5 provides a fluid pathway between at least one source of fluid and a subject. In the illustrated embodiment, the tubing provides a fluid pathway for two or more fluid sources, e.g., bags 12 and 13. A first inlet tube section 47 is connected at an inlet of the tubing 11 to bag 12 of feeding fluid and to valve mechanism 49. A second inlet tube section 51 is connected at an inlet of the tubing 11 to bag 13 of flushing fluid and to the valve mechanism. The valve mechanism 49 is operable to selectively permit flow of feeding fluid from bag 12 or flushing fluid from bag 13, or prevent any fluid flow communication from the feeding or flushing fluid bags 12, 13 past the valve mechanism. Thus, the valve mechanism 49 can be turned to three positions; a first position closes off all fluid flow from the inlet tube sections 47, 51 past the valve mechanism 49; a second position allows feeding fluid to flow from bag 12 past the valve mechanism, and a third position allows flushing fluid to flow from bag 13 past the valve mechanism. As previously stated, pump sets of different constructions may be used, for example a recertification set may be used to verify and/or correct the pump accuracy. The pump 1 can be configured to automatically recognize what kind of set is installed and to alter its operation to conform to that called for by the particular administration set. For example, the feeding set can have indicia (not shown) that can be linked to the pump and provide a signal that is representative of the type of pump set. Non-limiting examples, of such indicia include position-dependent magnetic interactive systems, electromagnetic signal processing systems, barcode systems, and combinations thereof. Still further, the pump 1 can be configured to recognize whether the tubing 11 is properly installed on the pump. In use, the feeding fluid bag 12 and flushing fluid bag 13 can be hung from a suitable support, such as an IV pole (not shown).

The pump 1 can be programmed or otherwise controlled for operation in a desired manner. For instance, the pump 1 can begin operation to provide feeding fluid from bag 12 to the subject. A user such as a care giver may select (for example) the amount of fluid to be delivered, the flow rate of the fluid and the frequency of fluid delivery. The pump 1 may have a controller 77 (FIG. 4) including a processor such as a microprocessor 79 that allows it to accept programming and/or to include preprogrammed operational routines, e.g., algorithm, that can be initiated by the user. The controller 77 may also be in communication with an administration set positioning sensor (not shown) that detects whether the administration feeding set 5 has been positioned properly. Other sensors (not shown), such as a sensor that determines the type of administration set that has been placed in the pump 1 and a flow monitoring sensor for detecting occlusions in the tubing 11 can be in communication with the controller 77 to facilitate accurate operation of the pump. The controller 77 may also be connected to the pump motor 27 for controlling its operation to actuate the valve mechanism 49 and the rotor 29. The pump motor 27 can operate the valve mechanism 49 and rotor 29 independently of each other. Other variants can involve actuating the valve mechanism 49 with the valve actuator or valve shaft 45 that is coupled to the controller 77, without being coupled to the pump motor 27. Thus, one or embodiments can involve energizing or controlling the pump in one or more flow configurations, with or without actuating the valve actuator.

If the pump 1 is to deliver feeding fluid from the bag 12 to the subject, the valve shaft 45 is rotated so that the valve mechanism 49 is moved to the second position in which fluid communication from the feeding fluid bag 12 past the valve mechanism is open and fluid communication from the flushing fluid bag 13 past the valve mechanism is closed. The pump 1 may be programmed or the user may input or select, for example, the amount of feeding fluid to be delivered to the subject, the flow rate at which the feeding fluid is to be delivered, and the frequency at which the feeding fluid is delivered. The amount of feeding fluid that is delivered to the subject is typically controlled by the number of rotations of the rotor 29 (in a counterclockwise direction as viewed in FIG. 2). In the exemplarily illustrated embodiment, the rotor 29 includes three rollers 43 so that each one-third of a rotation delivers one aliquot of fluid to the subject. The rotor can include additional rollers, each equispatially distributed about the periphery of the rotor. As each roller 43 first engages the tubing 11, it pinches off the tubing thereby closing off an amount of fluid forward (i.e., toward the subject) from the fluid coming from the feeding fluid bag 12. The roller 43 continues in the counterclockwise rotation which pushes the pinched-off volume of fluid forward of the roller, e.g., the aliquot, toward the subject. Finally, the leading roller 43 releases engagement with the tubing 11 at about the same time the trailing roller engages the tubing for pinching it off for delivering the next aliquot of fluid. Thus, when the microprocessor 79 receives a command to deliver a selected fluid flow rate, it calculates the number of rotations within a given period of time that will deliver a number of aliquots producing the desired flow rate. It is to be understood that other ways of changing rotor operation could be used to maintain a constant flow rate. The selected flow rate may be a rate that is input or selected by the doctor, nurse or other care giver, or may be a default feeding rate pre-programmed into the pump 1.

In one embodiment, if the pump 1 is to deliver flushing fluid from the bag 13 to the subject and effect a flushing configuration, the valve shaft 45 is rotated so that the valve mechanism 49 is moved to the third position in which fluid communication from the flushing fluid bag 13 past the valve mechanism is open and fluid communication from the feeding fluid bag 12 past the valve mechanism is closed. The amount of flushing fluid that is delivered through the tubing 11 is also controlled by the number of rotations of the rotor 29. The pump 1 may be programmed or the user may select (for example) the amount of flushing fluid to be delivered through the tubing, the rate at which the flushing fluid is to be delivered and the frequency or interval at which the flushing fluid is delivered. A flush cycle or flushing configuration period may operate at a programmed or selected interval after the feeding cycle, e.g., a feeding configuration period, is initiated. For example, if a flush interval of two hours is programmed or selected, the pump 1 may supply the selected volume of flush fluid at the selected rate two hours after initiating the feeding cycle. Subsequently, depending upon the length of the total feeding time, the flush cycle will be initiated or performed every two hours for the duration of the total feeding time. When the flush cycle is initiated it interrupts the initiated feeding cycle causing the amount of feeding fluid actually delivered to the subject in a given period to be less than the intended amount. The reduced amount of delivered feeding fluid may arise when the amount of time for completing the flushing cycle is included in the total feeding time. As a result, the volume of flushing fluid delivered through the tubing 11 is included in the calculation of the total amount of feeding fluid delivered, which may be undesirable. Therefore, the actual amount of feeding fluid delivered to the subject may be different from the calculated or intended volume of feeding fluid delivered. Specifically, the actual amount of feeding fluid delivered will be the intended amount of feeding fluid less the amount of feeding fluid that would have been delivered during the time flushing fluid is being delivered.

Accordingly, the controller 77 may comprise a timer 83 and a memory area 84 including a flush time compensator 85. In the illustrated embodiment, the flush time compensator 85 may include flush time compensation instructions 86 and flush time compensation functions 87. The timer 83 may be initiated in a suitable manner when a feeding cycle is initiated or performed for delivering feeding fluid from bag 12 through the tubing 11 and to the subject. The flush time compensator 85 may use this information along with additional parameters of the feeding and flush cycles to compensate for the volume of feeding fluid that is not delivered during the time the pump 1 is operated in a flush setting where the flushing fluid from bag 13 and not the feeding fluid is being delivered through the tubing 11.

The flush time compensator 85 can operate to adjust the flow rate for delivering the feeding fluid through the tubing 11 to account for the reduced or lost volume during the time the pump 1 operates in the flush setting, e.g., flushing configuration. This adjustment factor may be dependent on a selected or preprogrammed flow rate for the feeding fluid, and a volume, flow rate and flushing interval for the flushing fluid. More specifically, the controller 77 may employ the following function to determine an adjusted or compensated flow rate:

$$X_n = X/(1-((Y/R)/Z))$$

X is the selected flow rate for the feeding fluid. Y is a volume of the flushing fluid delivered through the pump set. R is a rate of flow for the flushing fluid. Z is a time interval for delivering the flushing fluid (e.g., every two hours). $X_n$ is an adjusted or compensated flow rate for the feeding fluid. It will be appreciated that the relationship of Y/R reduces to a time factor indicating the time for the flushing cycle. The function can be stored in the controller 77 so that when the factors are input into the pump 1 by the caregiver (or included in a preprogrammed feed setting), the microprocessor 79 can calculate the compensated flow rate $X_n$. The flush time compensator 85 provides computer-executable instructions 86 for use in calculating $X/(1-((Y/R)/Z))$.

For example, for a selected feeding fluid flow rate of 150 mL/hr, and a flush setting of 200 mL of flushing fluid every two hours with a flush rate of about 2000 mL/hr, flushing would interrupt the feeding for a total of 200 ml/2000 ml/hr or 0.1 hours (6 min.). Thus, 6 minutes of feeding fluid delivery time would be missed over each two hour flushing interval. This would total 15 mL of feeding fluid that is not delivered to the subject each flush interval. To compensate for the lost feeding fluid, the flow rate compensation algorithm can calculate the compensated flow rate $X_n$ for delivering the feeding fluid between flush intervals to achieve an average of the selected flow rate of 150 mL/hr. Thus, the compensated flow rate $X_n=150/(1-((200/2000)/2))=157$ mL/hr (rounded down to nearest mL/hr). Therefore, over the two hour flush interval, the flow rate for delivering the feeding fluid for the 1.9 hours (114 min) of feed delivery time would be 157 mL/hr resulting in 300 mL of feeding fluid delivered. Without the flow rate adjustment only 285 mL of feeding fluid would be delivered over the two hour flush interval.

In the above example, the flush cycle was assumed to occur within the initial two hour feeding time. It will be understood that if the flush cycle occurs after the initial two hour feeding time, the first two hours of feeding will occur at the selected rate of 150 mL/hr. However, a two hour flush interval may then result in the flush cycle occurring at the start of the second two hour feeding cycle. In this instance, the feed rate during the 1.9 hours (114 min.) after the flush cycle in the second two hour feeding cycle will increase to 157 mL/hr to account for the 6 minutes of flush time at the start of the second two hour feeding cycle. Subsequent feeding/flush cycles (configuration periods) would operate similarly.

Figure 5:
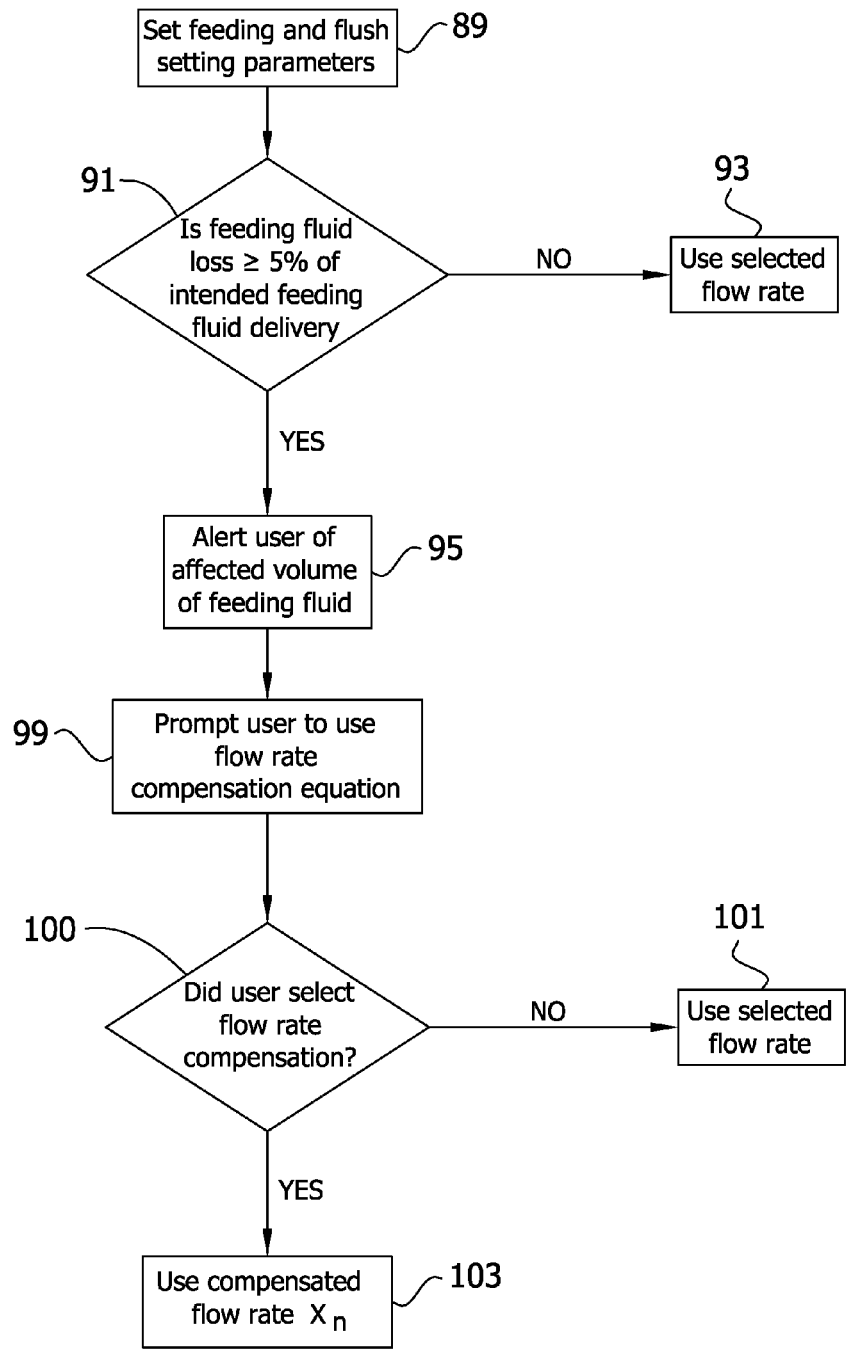
FIG. 5 is a flow chart of a flush time compensation routine in accordance with one or more aspects disclosed herein.

Referring now to FIGS. 4 and 5, the flush time compensation instructions 86 of the flush time compensator 85 used to account for flush cycle time are shown. The flush time compensation instructions 86 are machine readable instructions on any suitable medium, broadly identified as the memory area 84. These instructions can be executed by the microprocessor 79. After the selected flow rate X, flushing volume Y, flush rate R and flush interval Z are selected at block 89 (the flush parameters may also be preprogrammed in the feed setting), the flush time compensation instructions 86 first determines at decision block 91 if a flush time (Y/R) will result in a loss of a volume of the feeding fluid that is greater than or equal to an acceptable threshold value of the intended feeding fluid volume to be delivered during the flush interval. If the loss of feeding fluid volume is less than an acceptable threshold value, e.g., a threshold percentage, at 93 the selected flow rate X is used for the duration of the feeding cycle. In one embodiment the threshold percentage may be about 5% of the total intended feeding fluid volume. If the loss of feeding fluid volume is greater than or equal to the threshold percentage, at 95 the microprocessor 79 may display a notification on the display screen 21 or provide an alarm indication via LEDs 25 that the volume of feeding fluid may be less than the intended volume due to the programmed or selected flush cycle. At 99, the microprocessor 79 may prompt the user to use the flush time compensation. At 100, the microprocessor 79 may ask the user to decide whether to use the flush time compensation. If the user selects NO, at 101 the selected flow rate X may be used for the duration of the feeding cycle. If the user selects YES, at 103 the flow rate compensation function 87 may be used to calculate the compensated or adjusted flow rate $X_n$. The compensated flow rate can be used for at least a portion of the feeding cycle to ensure the intended volume of feeding fluid is delivered to the subject. The compensated flow rate $X_n$ may be incorporated before or after the initiation of an initial flush cycle. Further, the microprocessor 79 may automatically (i.e., without requiring user input) initiate the flow rate compensation function 87 if the loss of feeding fluid is determined to be greater than or equal to the threshold percentage.

Further variants can involve determining an intended or desired volume of the nutritional fluid, determining a minimum acceptable delivery volume as a product of the calculated delivery volume and a tolerance factor, and determining a modified fluid volume as result of time involved in the flushing configuration, which is based on the flush volume and the flush rate. For example, a desired fluid volume of 200 mL of nutritional fluid can be determined based on a user selected flow rate. If, for example, the minimum acceptable delivery volume is predefined to be within an acceptable tolerance, such as within 75% of the desired fluid volume, the minimum acceptable delivery volume is calculated to be 150 mL=(0.75)*(200 mL). If the processor determines that the modified fluid volume is greater than the minimum acceptable tolerance, then the processor regulates the pump at the selected feeding configuration. If the processor determines that the modified fluid volume is less than or equal to the minimum acceptable tolerance, then the processor regulates the pump at the compensated feeding configuration. Depending on one or more considerations, such as, but not limited to, the type of nutritional fluid, the subject or patient nutritional needs and limits, the acceptable tolerance can be in a range of from about 0.75 to about 0.99, or any value in a range of from 75% to 90%. For example, a critical patient may have a narrow nutritional tolerance requirement with an acceptable tolerance of 0.95 (or 95%) or greater.

At any time during the feeding cycle, flush parameters may be manually input by the user. In this instance, the microprocessor 79 will run the compensation instructions 86 as discussed above to determine whether a compensated flow rate is to be used. It will be understood that the period of the feeding cycle prior to the manual selection of the flush parameter would be operated under the selected feeding flow rate X, and a period of the feeding cycle after selection of the flush parameters may be operated under the compensated flow rate $X_n$. Moreover, the controller 77 may operate in instances where the first flush cycle does not occur for an interval after onset of feeding so that during the time up to the first flush cycle, the pump 1 is operated at the selected flow rate X and then after the first flush cycle is operated at the compensated flow rate $X_n$.

Thus it may be seen that the various objects and features are achieved by the various embodiments disclosed herein. The pump controller 77 has the flush time compensator 85 that allows the microprocessor 79 to compensate for the volume of feeding fluid that is not delivered during the time the pump 1 is operated in the flush setting where the flushing fluid and not the feeding fluid is being delivered through the tubing 11. Therefore, the subject can receive more accurate volume amounts of feeding fluid for a given feeding cycle.

Embodiments may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects may be implemented with any number and organization of such components or modules. For example, various features or aspects are not limited to the specific computer-executable instructions or the specific components or modules illustrated in the figures and described herein. Other embodiments may include different computer-executable instructions or components having more or less functionality than illustrated and described herein.

Further, the order of execution or performance of the operations in any of the embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of one or more aspects.

In operation, microprocessor 79 of the controller 77 executes computer-executable instructions such as those illustrated in the figures to implement one or more aspects disclosed herein. Any of the various aspects may also be practiced in distributed computing environments where tasks are performed by remote processing devices that are linked through a communications network. In a distributed computing environment, program modules may be located in both local and remote computer storage media including memory storage devices.

The preceding description is exemplarily directed to an enteral feeding system; however, one or more of the various aspects disclosed herein may be implemented in other pumping systems. Further, one or more of the various aspects may be implemented by retrofitting commercially available pumping apparatus including, for example, any one of the KANGAROO™ ePump enteral feeding pump and the KANGAROO™ Joey enteral feeding pump, available from Covidien LP, Mansfield, Mass. For example, the controller of any of the aforementioned enteral feeding pumps can be replaced or modified to include an algorithm with processor-executable instructions that perform any one of more of the features disclosed herein.

When introducing elements, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope, it is intended that all matter contained in the above description and shown in the accompanying drawings shall be interpreted as illustrative and not in a limiting sense.

What is claimed:

1. A pumping apparatus for use with a pump set to deliver fluid through the pump set to a subject, the pumping apparatus comprising:
   a pumping device capable of acting on the pump set to produce a fluid flow within the pump set; and
   a controller in communication with the pumping device for controlling operation of the pumping device in a feeding configuration for producing flow of a first fluid in the pump set and in a flushing configuration for producing flow of a second fluid different from the first fluid in the pump set, the controller including a processor and a memory, the processor configured to retrieve from the memory a selected flow rate and a desired fluid volume of the first fluid and at least one of a flush rate and a flush volume of the second fluid, the processor further configured to execute flush time compensator instructions provided by a flush time compensator of the controller for determining a compensated feeding configuration of the first fluid based on an amount of time the controller will operate the pumping device in the flushing configuration and the desired fluid volume of the first fluid.

2. The pumping apparatus as set forth in claim 1, wherein the compensated feeding configuration comprises a compensated flow rate of the first fluid to achieve the desired fluid volume of the first fluid based on an amount of time the controller will operate the pumping device in the flushing configuration, the compensated flow rate being different from the selected flow rate.

3. The pumping apparatus as set forth claim 2, wherein the flush time compensator calculates the compensated flow rate based on the equation: $Xn=X/(1-((Y/R)/Z))$, where X is the selected flow rate, Y is a volume of the second fluid to be delivered through the pump set in the flushing configuration, R is a rate of flow for the second fluid in the flushing configuration, Z is a time interval until initiation of the flushing configuration, and Xn is the compensated flow rate.

4. The pumping apparatus as set forth in claim 1, wherein the controller is configured to execute the flush time compensator if the controller determines that a duration of the flushing configuration will result in a volume of the first fluid not being delivered to the subject that is equal to or greater than an acceptable threshold value of the desired fluid volume of the first fluid.

5. The pumping apparatus as set forth in claim 4, wherein the controller is configured to execute the flush time compensator if the volume of the first fluid not delivered to the subject is determined to be at least 5% of the desired fluid volume of the first fluid.

6. The pumping apparatus as set forth in claim 4, wherein the controller is configured to output a notification recommending performance of the compensated feeding configuration if the volume of the first fluid not delivered is equal to or greater than the acceptable threshold value.

7. The pumping apparatus as set forth in claim 4, wherein the controller is configured to automatically use the compensated feeding configuration if the volume of the first fluid not delivered is equal to or greater than the acceptable threshold value.

8. The pumping apparatus as set forth in claim 7, wherein the compensated feeding configuration comprises a compensated flow rate of the first fluid, and wherein the controller is configured to operate the pumping device in a predetermined number of feeding configuration periods to deliver the desired volume of the first fluid, the controller automatically operates the pumping device in a first feeding configuration period at the selected flow rate of the first fluid and operates the pumping device in a second feeding configuration period at the compensated flow rate of the first fluid.

9. The pumping apparatus as set forth in claim 8, wherein the second feeding configuration period is shorter than the first feeding configuration period by an amount of time the controller operates the pumping device in the flushing configuration.

10. The pumping apparatus as set forth in claim 9, wherein the flush time compensator calculates the compensated flow rate based on a volume of the second fluid delivered through the pump set, a flow rate of the second fluid and a time interval until initiation of the next flushing configuration.

11. The pumping apparatus as set forth in claim 1, wherein the controller is configured to receive an input for initiating the flushing configuration of the pumping device, the controller configured to execute the flush time compensator and alter operation of the pumping device in the feeding configuration after receiving the input.

12. The pumping apparatus as set forth in claim 1, wherein the first fluid is a nutritional liquid and the second fluid is water.

13. The pumping apparatus set forth in claim 1, wherein the controller is configured to operate in the feeding configuration for a feeding configuration period and to operate in the flushing configuration for a flushing configuration period that is initiated at a flushing interval that interrupts the feeding configuration period.

14. A pumping apparatus for use with a pump set to deliver fluid through the pump set to a subject, the pumping apparatus comprising:
 a pumping device capable of acting on the pump set to produce a fluid flow within the pump set; and
 a controller in communication with the pumping device for controlling operation of the pumping device in a feeding configuration for producing flow of a first fluid in the pump set and in a flushing configuration for producing flow of a second fluid different from the first fluid in the pump set, the controller including a processor and a memory, the processor configured to retrieve from the memory a selected flow rate and a desired fluid volume of the first fluid and at least one of a flush rate and a flush volume of the second fluid, the processor further configured to execute flush time compensator instructions provided by a flush time compensator of the controller for determining a compensated feeding configuration of the first fluid based on an amount of time the controller will operate the pumping device in the flushing configuration and the desired fluid volume of the first fluid, wherein the controller is configured to execute the flush time compensator if the controller determines that a duration of the flushing configuration will result in a volume of the first fluid not being delivered to the subject that is equal to or greater than an acceptable threshold value of the desired fluid volume of the first fluid.

* * * * *